United States Patent
Cromwell et al.

(10) Patent No.: US 6,342,707 B1
(45) Date of Patent: Jan. 29, 2002

(54) LASER SCATTEROMETER WITH ADJUSTABLE BEAM BLOCK

(75) Inventors: Evan F. Cromwell, Redwood City; Johann F. Adam, Palo Alto, both of CA (US)

(73) Assignee: Katsina Optics, Inc., Milpitas, CA (US)

( * ) Notice: Subject to any disclaimer, the term of this patent is extended or adjusted under 35 U.S.C. 154(b) by 0 days.

(21) Appl. No.: 09/597,850

(22) Filed: Jun. 20, 2000

(51) Int. Cl.$^7$ .............................................. G01N 21/88
(52) U.S. Cl. .................. 250/559.4; 250/201.5
(58) Field of Search ............................ 250/201.5, 221, 250/216, 559.4, 559.45, 559.22, 237 R; 369/44.14, 44.11, 44.17, 44.23, 44.24; 356/446, 237.2, 237.3

(56) References Cited

U.S. PATENT DOCUMENTS

| | | | |
|---|---|---|---|
| 4,201,479 A | 5/1980 | Lardon | 356/445 |
| 4,269,518 A | 5/1981 | Rahn | 356/445 |
| 4,606,645 A | 8/1986 | Matthews et al. | 356/446 |
| 4,794,265 A | * 12/1988 | Quackenbos et al. | 250/572 |
| 4,873,430 A | 10/1989 | Juliana et al. | 250/225 |
| 5,062,021 A | 10/1991 | Ranjan et al. | 360/135 |
| 5,155,372 A | 10/1992 | Bowen et al. | 250/571 |
| 5,363,463 A | 11/1994 | Kleinerman | 385/123 |
| 5,416,594 A | 5/1995 | Gross et al. | 356/237 |
| 5,528,922 A | 6/1996 | Baumgart et al. | 73/1 J |
| 5,535,005 A | 7/1996 | Mukherjee-Roy et al. | 356/371 |
| 5,539,213 A | 7/1996 | Meeks et al. | 250/559.23 |
| 5,550,696 A | 8/1996 | Nguyen | 360/135 |
| 5,567,484 A | 10/1996 | Baumgart et al. | 427/555 |
| 5,586,040 A | 12/1996 | Baumgart et al. | 364/474.08 |
| 5,595,791 A | 1/1997 | Baumgart et al. | 427/554 |
| 5,608,527 A | 3/1997 | Valliant et al. | 356/371 |
| 5,631,408 A | 5/1997 | Baumgart et al. | 73/1.81 |
| 5,658,475 A | 8/1997 | Barenboim et al. | 219/121.77 |
| 5,703,692 A | 12/1997 | McNeil et al. | 356/445 |
| 5,729,640 A | 3/1998 | Castonguay | 382/321 |
| 5,768,076 A | 6/1998 | Baumgart et al. | 360/135 |
| 5,889,593 A | 3/1999 | Bareket | 356/445 |
| 6,031,615 A | 2/2000 | Meeks et al. | 356/381 |

FOREIGN PATENT DOCUMENTS

EP       0 652 554 A1    5/1995

* cited by examiner

Primary Examiner—Robert H. Kim
Assistant Examiner—Jurie Yun
(74) Attorney, Agent, or Firm—Skjerven Morrill MacPherson LLP; Edward C. Kwok; Michael J. Halbert (57) ABSTRACT

A laser scatterometer used, e.g., to detect defects on memory media, includes a beam block that can be finely adjusted so as to block specular light while maximizing the small angle scattered light that is received by the light detector. The beam block may be adjusted independently of the light detector or may be a masked beam block that is adjusted with the entire light detector. The light source produces a light beam that is focused so as to maximize the spot size on the object being tested while minimizing the spot size at the beam block, which advantageously maximizes the small angle scattered light while decreasing testing time. The large spot size at the object being tested permits detection of large defects. Thus, disks may be quickly tested, e.g., during the burnishing process, to determine if there are any large defects.

22 Claims, 5 Drawing Sheets

LASER SCATTEROMETER WITH ADJUSTABLE BEAM BLOCK

FIELD OF THE INVENTION

The present invention relates to optical scanners and in particular to a laser probe that uses scatterometry, for example, to detect defects on the surface of a memory disk.

BACKGROUND

A computer hard disk drive comprises a magnetic or optical memory disk mounted on a spindle, which is driven by a motor to rotate the magnetic disk at high speed. A read/write head, kept in close proximity to the surface of the rotating magnetic disk, reads or writes data on the magnetic disk. The read/write head is separated from the surface of the magnetic disk by an air bearing created by the high-speed rotation of the magnetic disk. The read/write head flies on this air bearing, e.g., at a height of approximately one microinch. The closer the read/write head is to the surface of the magnetic disk, the more information may be written on the disk. Thus, it is desirable for the read/write head to fly as close as possible to the surface of the magnetic disk.

Typical magnetic disks comprise an Al substrate, a NiP layer which is plated on the Al, polished and then textured, an underlayer (e.g. Cr or NiP) sputtered on the plated NiP layer, a thin film of magnetic recording material (typically a Co alloy) sputtered on the underlayer, a protective overcoat sputtered on the magnetic film and a lubrication layer formed on the overcoat. Magnetic disk manufacturing specifications typically require that asperities and depressions on a magnetic disk are smaller than a certain size. Although magnetic disks are typically textured to have a specified roughness, there has been a trend in the industry to make magnetic disks smoother and smoother. Presently, some magnetic disks are specified to have a roughness less than or equal to about 10 Å (1 nm). As the specified roughness is decreased, the size of the asperity or depression that can be tolerated is decreased.

The precision with which the read/write head flies over the magnetic disk requires that care is taken during manufacturing to assure that there are no protrusions or asperities on the disk surface that may interfere with the read/write head. A protrusion on the surface of the disk that contacts the read/write head during use may damage the head or the disk.

Accordingly, during manufacturing of magnetic or magnetic-optical disks, tests are performed with "media certifiers" using, e.g., glide heads, to ensure that there are no defects, such as asperities, voids or contamination, that might interfere with the read/write head. Accurate testing of disks for such defects assures that the disk manufacturer does not unnecessarily reject good quality disks or pass on poor quality disks that may later fail.

Certifying disks using glide heads can be a time consuming task. Each disk must be individually mounted on a spindle. The disk is rotated at high speed, while a burnish head is moved across the surface to remove loose debris and then a glide head is moved across the surface of the disk to check for asperities or defects. The disk is then dismounted from the spindle. If the disk is found to have an unacceptable defect, the disk is rejected. Typically, however, before rejecting the disk, the disk is retested. A different media certifier is sometimes used to retest the disk, which requires mounting the disk on a different spindle, rotating the disk while burnish and glide heads move across the surface and dismounting the disk. Consequently, a disproportionate amount of time may be spent retesting a defective disk.

SUMMARY

A laser scatterometer, in accordance with the present invention, may be used to detect defects on objects such as memory media. The laser scatterometer includes a light source that produces a light beam that is incident on the object being tested. The light reflected from the object has two components, a specular component and a scattered component, which is caused, e.g., by defects. A photodetector, which receives the reflected light, includes a light detector (such as a photodiode) and a beam block. The beam block is adjustable so that the specular component can be blocked while minimizing interference with the scattered component. In one embodiment, the beam block is masked on the lens of the light detector and the entire photodetector is moved so that the specular light is incident on the beam block. Because the beam block can be finely adjusted to block only the specular light, the beam block may be adjusted to permit more small angle scattered light to pass to the light detector than conventional systems. The light source, such as a laser or laser diode, produces a beam of light that is focused so as to minimize the spot size at the beam block while maximizing the spot size on the surface of the object being tested. Consequently, the object may be tested quickly and the small angle scattered light is maximized.

Because a large spot size is used at the surface of the object, e.g., the rotating disk, the laser scatterometer may be used at the same time as the burnishing process, immediately before glide testing. The large spot size is used to detect large defects. Moreover, because the small angle scattered light signal is maximized, defects (e.g., sub-bumps) that are conventionally detected only with glide testing, may be detected with the laser scatterometer. By using the laser scatterometer during the burnishing process, disks with large defects may be immediately rejected without requiring additional time-intensive testing of the defective disk. The remaining disks, which were not rejected, can then undergo additional testing, e.g., glide testing, for smaller defects. Consequently, eliminating clearly defective disks by using the laser scatterometer during the burnishing process will increase the throughput in the glide testing process and eliminate the time that would have been required to test these defective disks.

BRIEF DESCRIPTION OF THE DRAWINGS

These and other features of the invention will be understood from the description below and the claims appended hereto taken together with the drawings of illustrative embodiments and features of the invention, wherein:

DETAILED DESCRIPTION

A laser scatterometer, in accordance with the present invention, is used to detect defects, such as asperities, voids or contamination over the entire surface of a rotating media disk, such as a magnetic or magneto-optical disk. In one embodiment, the laser scatterometer produces a large unfocused spot on the surface of the disk. The large spot advantageously covers a large area over the surface of the disk thereby minimizing the testing time. While the large unfocused spot size causes a reduced sensitivity in the laser scatterometer, the sensitivity is adequate to detect large defects. Thus, the laser scatterometer may be used to quickly detect large defects, for example, during the burnishing process. Consequently, disks with large defects may be eliminated during the burnishing process thereby reducing the number of disks to be glide tested and increasing the yield in the glide tests.

In another embodiment of the present invention, an adjustable beam block is used to block the specular light and maximize the small angle scattered light signal that is received by the light detector. The adjustable beam block advantageously permits the laser scatterometer to be mounted and calibrated with a high degree of accuracy, which permits the use of a very small beam block. With the use of a small beam block, small angle scattered light is maximized, which permits detection of certain defects that are typically detected with only glide heads.

Figure 1:
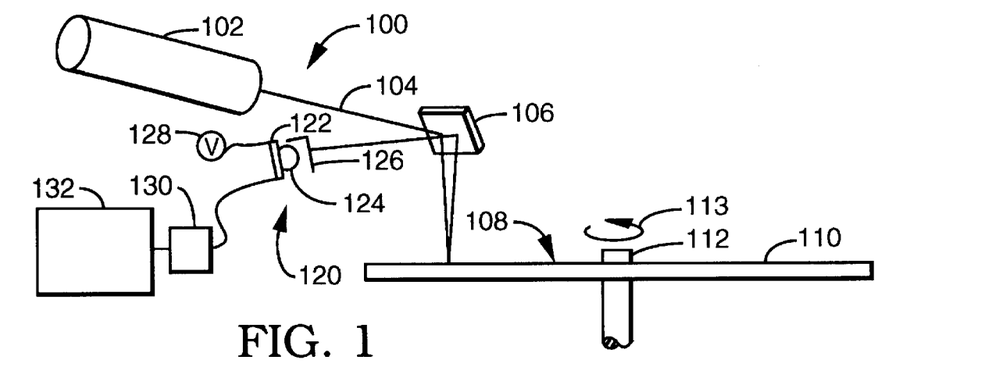
FIG. 1 shows a schematic view of a laser scatterometer that uses a beam of light to detect defects on the surface of a rotating disk, in accordance with an embodiment of the present invention.

FIG. 1 shows a schematic view of a laser scatterometer 100 that uses a beam of light to detect defects on the surface 108 of a rotating disk 110. As shown in FIG. 1, laser scatterometer 100 includes a light emitting laser source 102, which may be a laser or laser diodes, such as model LHWB 670-5 manufactured by Power Technology, Inc. Laser source 102 emits a beam 104 of light that may be coherent, and for example, has a desired wavelength of 670 nm. The beam 104 is reflected by a mirror 106 towards the surface 108 of the disk 110, which is rotating about a spindle 112 as indicated by arrow 113.

Laser scatterometer 100 also includes a photodetector 120 that receives the beam 104 after it is reflected off the surface 108 and is directed, via mirror 106 or by a different mirror (not shown), towards the photodetector 120. As shown in FIG. 1, photodetector 120 includes a photodiode 122, a collection lens 124 mounted on the photodiode 122, and a beam block 126 that is used to block the specular light reflected from surface 108. A voltage source 128 provides a voltage to the photodiode 122. The signal from the photodiode is conditioned by conditioning electronics represented by block 130, which may for example include a preamplifier and a band pass filter. The band pass filter may be adjusted to pass the desired frequency, e.g., 10 to 60 kHz, and is used to increase the signal to noise ratio. If desired, other conditioning electronics may be used such as a lock in amplifier. Appropriate conditioning electronics, including band pass filter, may be purchased from Z-Tek, Inc., located in Fremont, California, or Phase Metrics, Inc., located in San Diego, California, and should be compatible with Cambrian Testers. The output signal from the conditioning electronics 130 is received by an appropriate detection device, such as a conventional media certifier, such as the type manufactured by Phase Metrics or Hitachi.

Figure 2A:
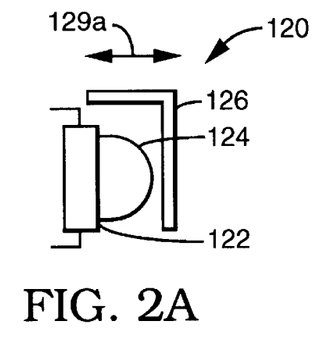
FIGS. 2A and 2B show schematically side and front views, respectively, of a photodetector with an adjustable beam block.
Figure 2B:
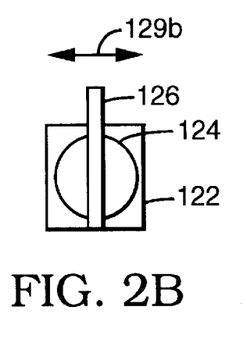

FIGS. 2A and 2B show schematically side and front views, respectively, of photodetector 120 with adjustable beam block 126. Adjustable beam block 126 is a small rod, for example, a wire that is coupled to set screws. As illustrated in FIGS. 2A and 2B, beam block 126 may be moved away and towards photodiode 122, as indicated by arrow 129a, and from side to side of photodiode 122, as indicated by arrow 129b. Beam block 126 may move, e.g., approximately 0.1 inches away from collector lens 124 and approximately ±0.050 inches to the sides of the center of collector lens 124. Ideally, beam block 126 will be centered and in contact with collector lens 124. However, during calibration of the device, it may be necessary to adjust beam block 126 away from this position to block the specular light. Because beam block 126 can be finely adjusted, beam block 126 may have a width of approximately 0.040 inches, which is approximately twice the diameter of the spot focused on beam block 126, approximately 0.020 inches. In some embodiments, the beam block 126 may have dimensions that are approximately the same size as the spot. Further, beam block 126 may be finely adjusted so that the spot focused on the beam block 126 is close to the edge of the beam block and in one embodiment is focused so that a small portion of the spot, e.g., 1% to 5%, is incident outside the edge of the beam block 126. Consequently, beam block 126 will permit scattered light with very small angles to pass and to be detected by the photodiode 122.

Figure 3A:
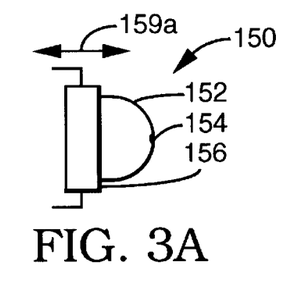
FIGS. 3A and 3B show schematically side and front views, respectively, of a photodetector with a masked beam block that may be adjusted, along with the photodetector, in accordance with another embodiment of the present invention.
Figure 3B:
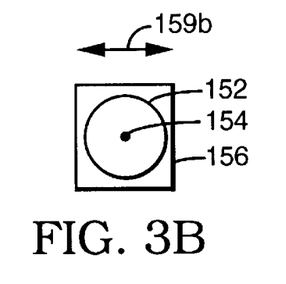

FIGS. 3A and 3B show schematically side and front views, respectively, of a photodetector 150 that may be used in accordance with another embodiment of the present invention. As shown in FIGS. 3A and 3B, the center of the collector lens 152 is masked off to act as the beam block 154. With the beam block 154 on the collector lens 152, the entire photodetector 150, including photodiode 156, collector lens 152 and beam block 154 are adjustable, as indicated by arrows 159a and 159b. Again, because the beam block 154 can be accurately positioned to block the specular light, the diameter of beam block 154 is approximately the same as the diameter of the spot focused on beam block 154. Accordingly, beam blocks 126 and 154 are approximately the same size as the specular light, the beam blocks 126 and 154 block only the specular light and permit small angle scattered light, i.e., light that is scattered but has a small angle relative to the specular light, to be received by the photodiode 122 and 156.

Figure 3C:
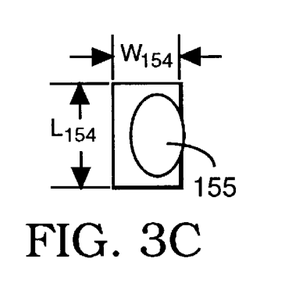
FIG. 3C shows a front view of a beam block with a desired percentage of a light spot incident on the beam block.

FIG. 3C shows a front view of beam block 154 with a light spot 155 incident on beam block 154. As shown in FIG. 3C, beam block 154 has length $L_{154}$ of approximately 0.100 inches and a width $W_{154}$ of approximately 0.040 inches, whereas the light spot is approximately 0.020 inches in diameter. Thus, the width of beam block 154 is approximately twice the size of the diameter of spot 155. As shown in FIG. 3C, the beam block 154 can be adjusted so that a small portion of the light spot 155, e.g., 1% to 5%, is incident outside the beam block 154. The beam block 154 may be calibrated by adjusting the beam block so that the photodiode 156 produces a signal indicative of the desired percentage of the intensity of the light beam 104, i.e., the ratio of the voltage signals from the photodiode 156 caused by the partial beam and the full beam ($V_{partial\ beam}/V_{full\ beam}$).

Figure 4A:
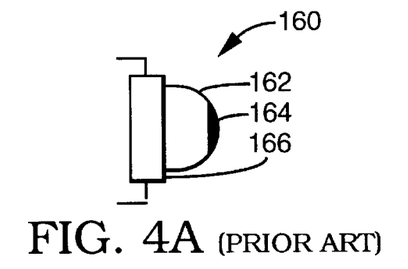
FIGS. 4A and 4B show schematically side and front views, respectively, of a conventional photodetector that does not have an adjustable beam block.
Figure 4B:
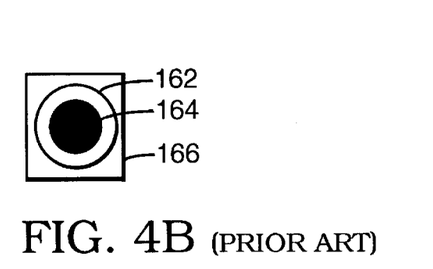

Because beam blocks 126 and 154 can be adjusted so that the light beam is focused on them, beam blocks 126 and 154 may be very small relative to beam blocks used in conventional scatterometers. FIGS. 4A and 4B show schematically side and front views, respectively, of a conventional photodetector 160, which does not have an adjustable beam block. As shown in FIGS. 4A and 4B, photodetector 160 includes a photodiode 166 and has a masked off area on the collector lens 162 that acts as the beam block 164. To calibrate a conventional laser scatterometer, the laser is rotated or otherwise adjusted until the laser beam is incident at some place on the beam block 164. The calibration of a conventional laser scatterometer probe is imprecise, and thus requires a large beam block 164 to ensure that the specular light will be incident on beam block 164. Consequently, a conventional photodetector 160 will not receive small angle scattered light.

Figure 5:
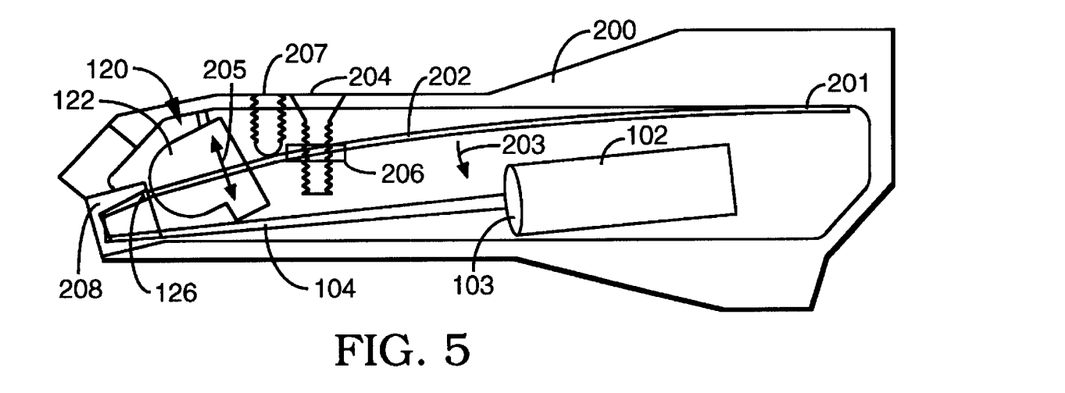
FIG. 5 shows a top cut-away view of a laser scatterometer with adjustable beam block in a housing.

FIG. 5 shows a top cut-away view of a housing 200 containing the laser scatterometer 100, with the laser diode 102 with a lens 103 and photodetector 120 mounted to the housing 200, for example, using an appropriate epoxy such as a 5 minute epoxy. As shown in FIG. 5, beam block 126 is an integral part of a flexible arm 202, which has one end 201 mounted to housing 200 in an appropriate manner, such as a 5 minute epoxy or a bolt. In one embodiment, the beam block 126 is mounted to flexible arm 202. The flexible arm 202 is biased towards the laser diode 102, as indicated by arrow 203. A set screw 204 is coupled to flexible arm by, e.g., a bolt 206, and is used to adjust the position of beam block 126 as desired, as indicated by arrow 205. A stop bolt 207 is used to prevent flexible arm 202 from being adjusted too far. Thus, as shown in FIG. 5, laser diode 102 produces a beam of light 104 that reflects off a mirror 208, or a coated prism, which may be mounted on or an integral part of housing 200. The beam of light 104 is incident on and reflects off the surface of the disk (not shown), reflects off mirror 208 towards photodetector 120. All or a portion of the specular light is blocked by beam block 126, while the scattered light is received by the photodiode 122.

Figure 6:
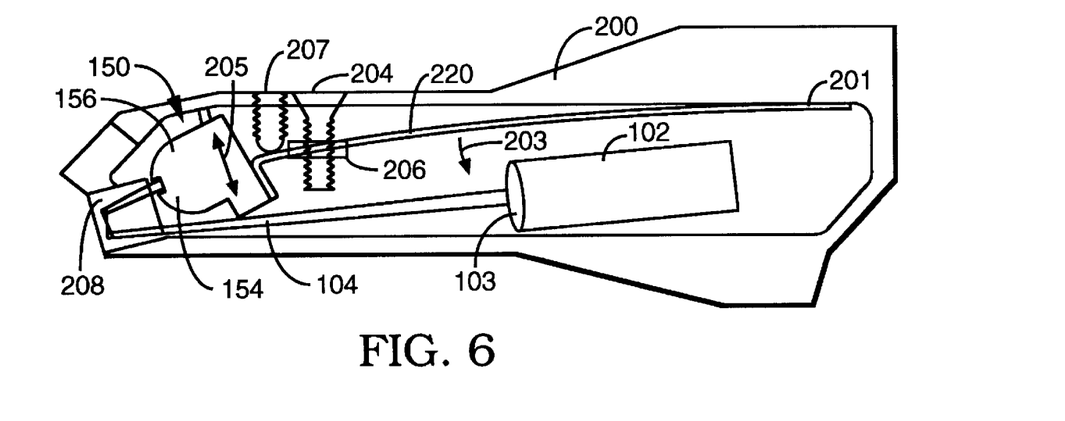
FIG. 6 shows a top cut-away view of a laser scatterometer with adjustable beam block in accordance with another embodiment of the present invention in a housing.

FIG. 6 shows a top cut-away view of housing 200 with a flexible arm 220 mounted to the photodiode 156. Thus, FIG. 6 is similar to FIG. 5, like designated elements being the same, except flexible arm 220 moves the entire photo diode 156 to properly adjust the beam block 154.

It should be understood that while FIGS. 5 and 6 show the use of a set screw 204 to manually adjust the position of the beam blocks 126 and 154, other devices may be used to adjust beam block as will be apparent to those of ordinary skill in the art. For example, in one embodiment, an electrical feed back mechanism may be used to control an actuator to adjust beam block to minimize or to control the percentage of the specular light based on the signal received by the photodetector.

Figure 7:
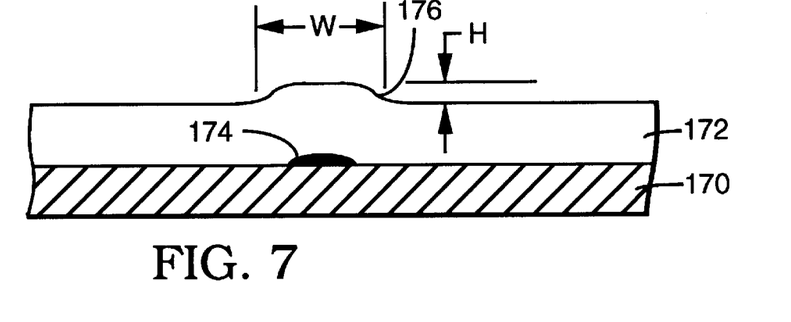
FIG. 7 shows a cut-away side view of a defect referred to as a "sub-bump" that may be detected using small angled scattered light signals.

Because photodetectors 120 and 150 can detect small angle scattered light, certain defects that are conventionally detected only with glide heads can be detected with laser scatterometer 100. FIG. 7 shows a cut-away side view of a defect referred to as a "sub-bump." As shown in FIG. 7, a disk substrate 170, which is typically aluminum, is covered with a NiP layer 172. If a defect 174 is present on substrate 170 prior to depositing NiP layer 172, when layer 172 is deposited it will cover defect 174 and form a raised area, sometimes called a "sub-bump 176." Sub-bumps typically have a width W of 10 μm to 50 μm and a height H of 25 nm to 50 nm. Because sub-bumps have gently sloping sides, light is typically scattered off sub-bumps at small angles. Consequently, photodetectors with non-adjustable and relatively large beam blocks, such as that shown in FIGS. 4A and 4B, block small angled scattered light, and thus cannot detect sub-bumps. Photodetectors 120 and 150, on the other hand, maximize the small angle scattered light, which advantageously permits detection of defects such as sub-bumps.

Figure 8:
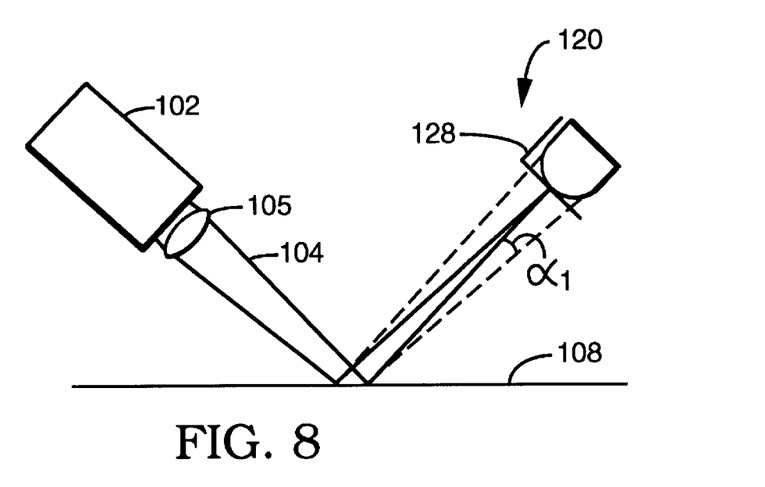
FIG. 8 shows a schematic view of a laser scatterometer with a beam of light with a maximum spot size on the surface of a rotating disk and a minimal spot size at the beam block.

FIG. 8 shows a schematic view of laser scatterometer 100 with a beam of light 104 emitted by a diode laser 102 and reflecting off the surface 108 of a rotating disk. As shown in FIG. 8, a lens 105, or series of lenses focuses the beam 104, such that the beam is unfocused at the plane of the surface 108 and is focused on photodetector 120. The reflected light beam 104 may be approximately focused on beam block 128, because beam block 128 may have to be adjusted to completely block the specular light. As discussed above, the specular light (shown with solid lines) is blocked by beam block 128. Thus, alignment conditions maximize the spot size on the surface 108 while minimizing the spot size at beam block 128. Photodetector 120 receives the light that is scattered from the surface 108, as indicated by the dotted lines, which forms a maximum angle a1 with the specular light as indicated in FIG. 8.

Figure 9:
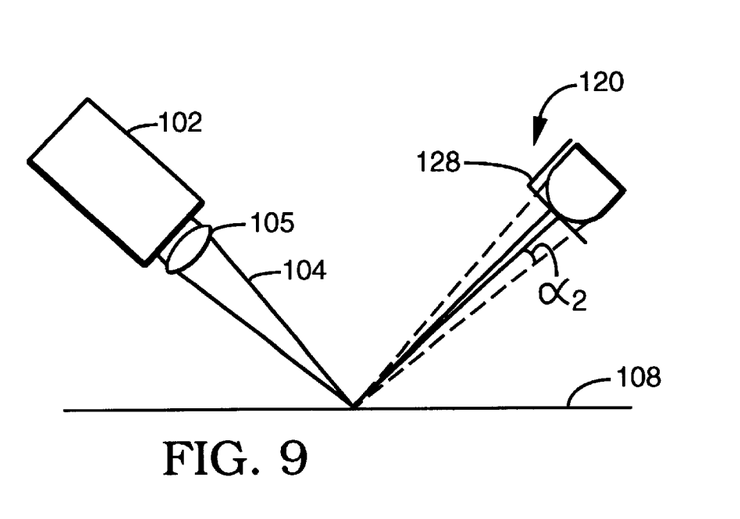
FIG. 9 shows a schematic view of a laser scatterometer with a beam of light with a minimal spot size on the surface of the rotating disk.

For the sake of comparison, FIG. 9 shows laser scatterometer 100 with the light beam focused on the surface 108. Consequently, the spot size on the surface 108 is minimized while the spot size at beam block 128 is maximized. As indicated in FIG. 9, the scattered light, indicated by dotted lines, forms a maximum angle $\alpha_2$ with the specular light. Holding all other conditions the same, the maximum angle $\alpha_1$ shown in FIG. 8 is greater than the maximum angle $\alpha_2$, shown in FIG. 9 and thus the small angle scattered light received with the unfocused condition shown in FIG. 8 is increased. The larger maximum angle $\alpha_2$, shown in FIG. 9 may be used advantageously to detect small defects.

In addition, with the unfocused condition as shown in FIG. 8, the area of coverage of light beam 104 is increased. Consequently, the entire disk surface 108 may be covered in less time than with the use of a focused beam.

Figure 10:
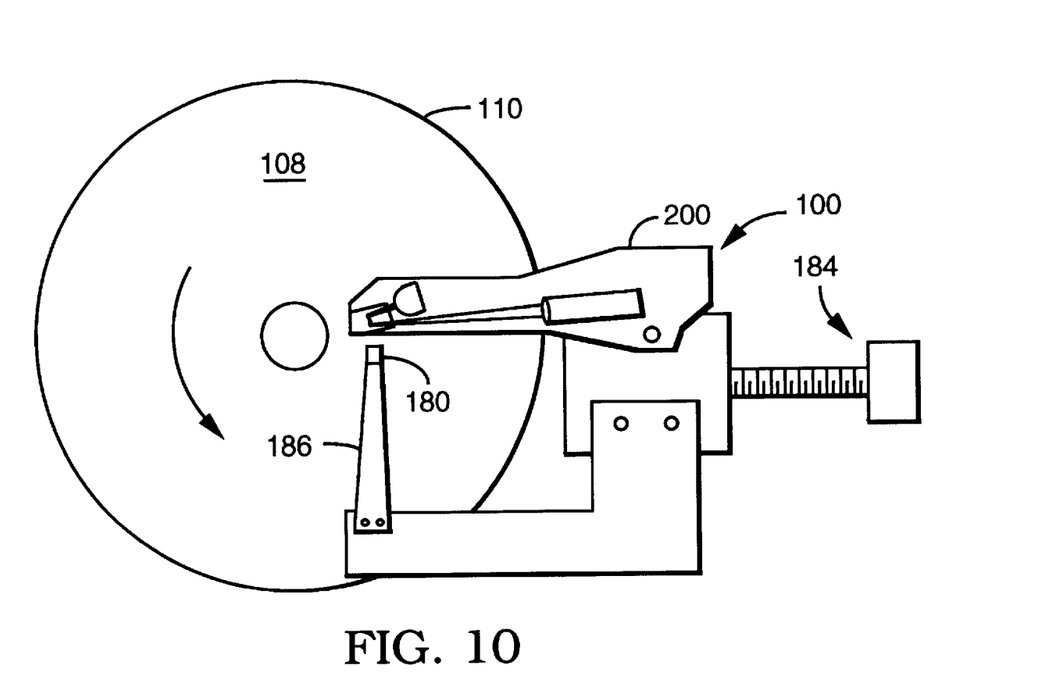
FIG. 10 shows the laser scatterometer being used during the burnishing processes.

In an embodiment of the present invention, the laser scatterometer 100 is used to test a disk during the burnishing of the disk. FIG. 10 shows the housing 200 of laser scatterometer 100 and a burnishing head 180 over the surface 108 of disk 110 during the burnishing process. Laser scatterometer 100 in housing 200 is incorporated into the erase magnet assembly on a conventional burnishing apparatus. Burnishing head 180, which may be any conventional burnishing head, is also mounted on a suspension arm 186. The laser scatterometer 100 and burnishing head 180 are moved with an actuator 184, which may be, for example, a stepper motor. Actuator 184 moves the burnishing head 180 and laser scatterometer 100 from the inside diameter to the outside diameter of disk 110.

The unfocused spot size produced by laser scatterometer 100 on the surface 108 of disk 110 should have a diameter that is at least as large as the radial step size and pitch of the burnishing head 180. Because the spot size is approximately the same as the step size of the burnishing head, the laser scatterometer 100 can test the entire surface of the disk 110 in the same amount of time that burnishing head burnishes the surface 108. Consequently, disk 110 can be tested for defects with laser scatterometer 100 at no additional cost of time.

Accordingly, laser scatterometer 100 is used to detect large defects on the disk 110, including sub-bumps, during the burnishing process. A disk with such defects can then be failed without requiring that disk to be glide tested. Consequently, the number of unqualified disks to be glide tested is reduced, which will increase yield of the glide test.

Figure 11:
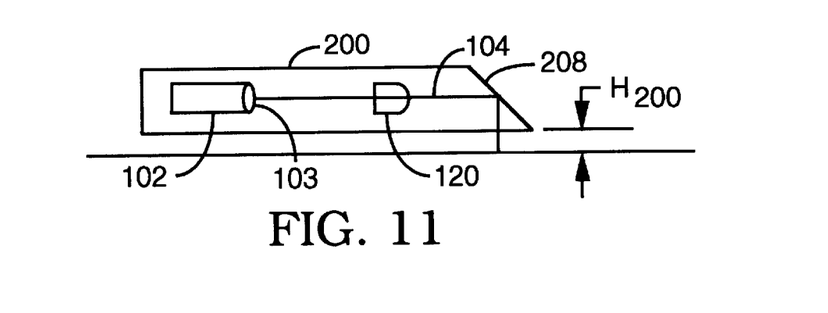
FIG. 11 show a side view of a housing with a laser scatterometer mounted over the surface of a disk.

FIG. 11 shows a side view of housing 200 with laser scatterometer 100 mounted over the surface 108 of disk 110. Laser diode 102 is shown positioned inside housing 200 along with beam 104 reflecting off a mirror 208 and received by photodetector 120. As shown in FIG. 11, housing 200 is mounted a height $H_{200}$ above surface 108, which is approximately 0.2 inches. The use of coherent light advantageously permits independent control over the spot size of the laser scatterometer 100. Consequently, laser scatterometer 100 in housing 200 may be mounted above surface 108 with a relatively large separation between the device and the surface 108 compared to devices that use non-coherent light. For example, devices that use non-coherent light to detect defects typically have a separation with the disk of only 0.05 inches. The large separation that is advantageously permitted with the use of laser scatterometer 100 reduces the risk of impact between the scatterometer device and the surface 108 of disk 110. Because a crash may result in damage to the disk and may either damage the scatterometer or require recalibration of the scatterometer, resulting in downtime, a large separation is clearly desirable.

In addition, with the use of photodetector 120 and adjustable beam block 126 or 154, the laser scatterometer 100 may be calibrated in situ. Thus, the position of the housing 140 and laser scatterometer 100 relative to the surface 108 may be established prior to adjusting the beam block 126 or 154. Consequently, the angle of incidence of the beam 104 relative to the surface 108, which is ideally normal as shown in FIG. 11, may be maintained while the laser scatterometer 100 is calibrated.

Figure 12:
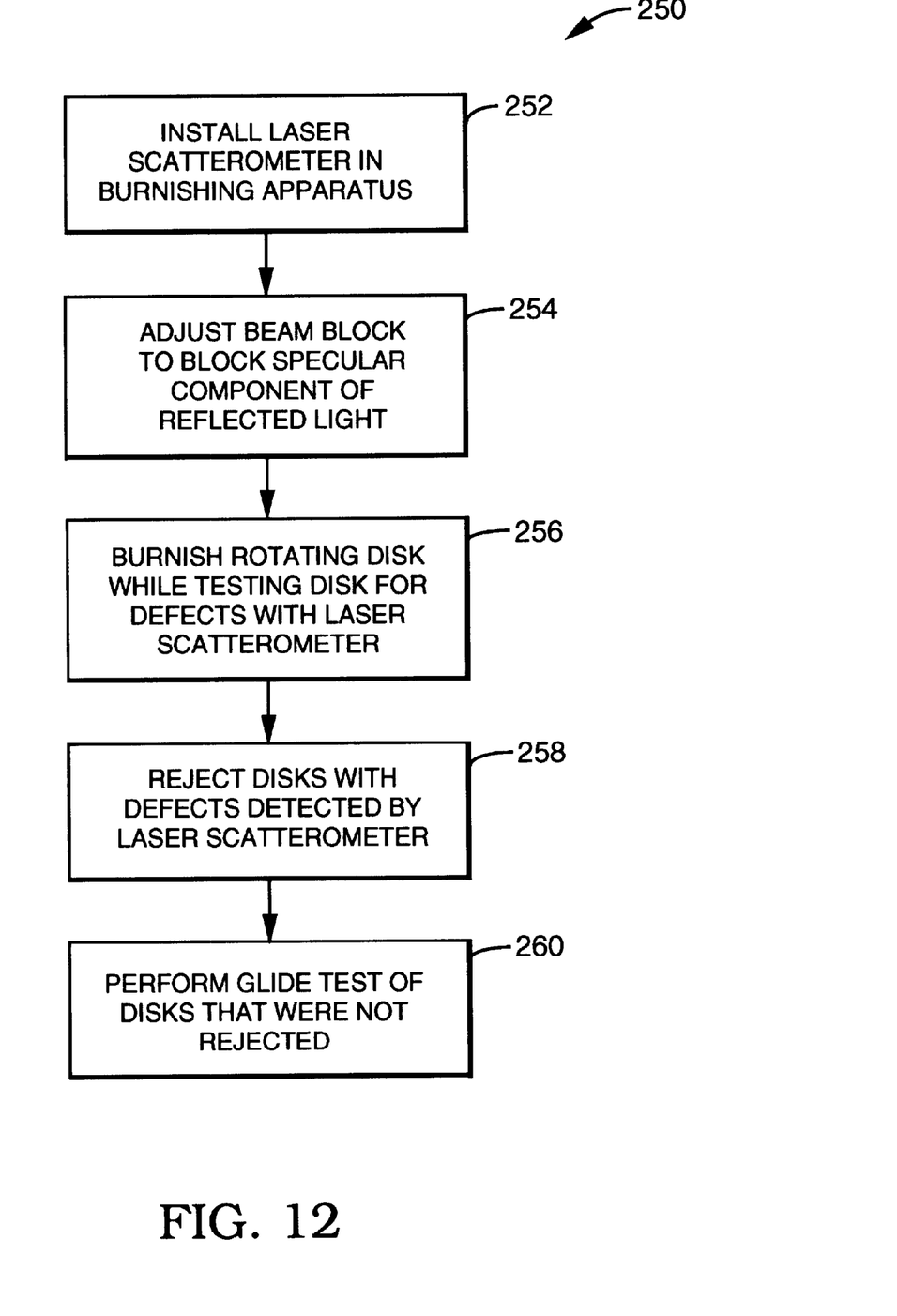
FIG. 12 is a flow chart describing the process of burnishing a disk while testing the disk for defects with the laser scatterometer.

FIG. 12 is a flow chart 250 of a method of using laser scatterometer 100 during the burnishing process. As shown in FIG. 12, the laser scatterometer is installed in the burnishing apparatus (block 252). The beam block is adjusted to block the specular component of the reflected light, while permitting the scattered component of the reflected light to pass (block 254). The beam block may be moved independently of the light detector or may be a masked beam block with the entire light detector (with masked beam block) moved so that the beam block blocks the specular light. The disk is rotated and burnished while the laser scatterometer tests the disk for defects (block 256). Any disks with defects detected by the laser scatterometer are rejected (block 258). A glide test, or other appropriate test, is then performed on the disks that were not rejected (block 260). Because the laser scatterometer uses a large spot size at the surface of the disk, only large defects will be detected. Thus, the glide test is performed to ensure there are no smaller defects.

Although the present invention is illustrated in connection with specific embodiments for instructional purposes, the present invention is not limited thereto. Various adaptations and modifications may be made without departing from the scope of the invention. For example, the size and configuration of the adjustable beam block may be varied, for example, to maximize the small angle scattered light. Moreover, the type of coherent light source may be altered. Accordingly, all such changes come within the scope of the invention as recited below.

What is claimed is:

1. A laser scatterometer for testing a rotating disk for defects, said laser scatterometer comprising:
   a light source for producing a light beam that reflects off a surface of said rotating disk, the reflected light beam including a specular component and a scattered component;
   a photodetector for receiving said reflected light beam, said photodetector comprising:
   a light detector; and
   an adjustable beam block that blocks said specular component, said adjustable beam block being adjustable relative to said reflected light beam.

2. The laser scatterometer of claim 1, wherein said adjustable beam block has a width that is approximately the same size as the spot produced by said specular component.

3. The laser scatterometer of claim 1, wherein said adjustable beam block has a width that is approximately twice the size of the spot produced by said specular component.

4. The laser scatterometer, of claim 1, wherein said light source comprises a laser diode and a lens for focusing said light beam, said light beam being unfocused at said surface of said rotating disk.

5. The laser scatterometer of claim 4, wherein said light beam is focused at said photodetector.

6. The laser scatterometer, of claim 1, wherein said light source comprises a laser diode and a lens for focusing said light beam, said light beam being focused at said surface of said rotating disk.

7. The laser scatterometer of claim 1, wherein said adjustable beam block is a rod coupled to at least one set screw, said adjustable beam block being movable away from and towards said light detector and from side to side of said light detector.

8. The laser scatterometer of claim 1, wherein light detector is a photodiode with a lens coupled to said photodiode, said adjustable beam block being a masked area of said lens, said photodetector being coupled to at least one set screw, said adjustable beam block being adjusted with said photodiode and lens.

9. A method comprising:
   providing a laser scatterometer over the surface of a disk, said scatterometer having an adjustable beam block;
   producing a beam of light that reflects off said surface of said disk and is incident on a photodetector;
   calibrating said laser scatterometer by adjusting said adjustable beam block to block a desired percentage of the specular light reflected off said surface of said disk; and
   testing a disk for defects with said laser scatterometer.

10. The method of claim 9, wherein testing a disk for defects comprises:
    producing a beam of light that is unfocused on said surface and that reflects off said surface and is scattered by defects present on said surface; and
    detecting the light that is scattered by defects on said surface.

11. The method of claim 9, wherein the desired percentage is 100% of the specular light.

12. The method of claim 9, wherein the desired percentage is less than or equal to 5% of the specular light.

13. The method of claim 9, wherein testing a disk for defects with said laser scatterometer is performed while burnishing the surface of said disk.

14. The method of claim 9, wherein adjusting said adjustable beam block comprises moving an adjustable beam block relative to the specular light.

15. The method of claim 14, wherein adjusting said adjustable beam block comprises moving an adjustable beam block relative to the specular light and a photo diode.

16. An apparatus comprising:

a housing;

a light source mounted to said housing, said light source producing a light beam that is directed to be incident on and reflected off an object to be tested for defects;

a beam block for blocking the specular component of the light reflected off said object;

a light detector for receiving the scattered component of the light reflected off said object; and means for moving said beam block so that said specular component is incident on said beam block.

17. The apparatus of claim 16, further comprising at least one mirror that directs said light beam to be incident on and reflected off said object, and that directs said light reflected off said object to said light detector.

18. The apparatus of claim 16, further comprising a first mirror that directs said light beam to be incident on and reflected off said object, and a second mirror that directs said light reflected off said object to said light detector.

19. The apparatus of claim 16, wherein said means comprises at least one set screw coupled to said beam block that moves said beam block.

20. The apparatus of claim 16, wherein said means comprises at least one set screw coupled to said light detector and said beam block, said at least one set screw moves both said light detector and said beam block.

21. The apparatus of claim 16, wherein said light beam is focused to have a minimal spot size at said beam block.

22. The apparatus of claim 21, wherein said light beam is focused to maximize the spot size on said object while having a minimal spot size at said beam block.

* * * * *